United States Patent
Kramer et al.

(10) Patent No.: US 9,263,862 B2
(45) Date of Patent: Feb. 16, 2016

(54) METHOD FOR OPERATING AN ELECTRICAL APPARATUS

(71) Applicants: Axel Kramer, Wettingen (CH); Thomas Alfred Paul, Waedenswil (CH)

(72) Inventors: Axel Kramer, Wettingen (CH); Thomas Alfred Paul, Waedenswil (CH)

(73) Assignee: ABB TECHNOLOGY AG (CH)

( * ) Notice: Subject to any disclaimer, the term of this patent is extended or adjusted under 35 U.S.C. 154(b) by 0 days.

(21) Appl. No.: 14/304,591

(22) Filed: Jun. 13, 2014

(65) Prior Publication Data

US 2014/0321031 A1     Oct. 30, 2014

Related U.S. Application Data

(63) Continuation of application No. PCT/EP2012/075207, filed on Dec. 12, 2012, and a continuation of application No. PCT/EP2012/067215, filed on Sep. 4, 2012, and a continuation of application No. PCT/EP2012/051688, filed on Feb. 1, 2012, and a continuation of application No. PCT/EP2011/072510, filed on Dec. 13, 2011.

(51) Int. Cl.
| | |
|---|---|
| *H02B 13/065* | (2006.01) |
| *G01N 33/00* | (2006.01) |
| *H01H 33/56* | (2006.01) |

(52) U.S. Cl.
CPC ........ *H02B 13/0655* (2013.01); *G01N 33/0032* (2013.01); *G01N 33/0027* (2013.01); *H01H 2033/566* (2013.01)

(58) Field of Classification Search
CPC .......... H01H 33/563; H01H 2033/566; H01H 2033/567; G01N 33/0031; G01N 33/0032; H02B 13/0655
See application file for complete search history.

(56) References Cited

U.S. PATENT DOCUMENTS

| | | | | |
|---|---|---|---|---|
| 3,934,454 A | * | 1/1976 | Simo | G01N 33/0004 374/143 |
| 4,110,580 A | * | 8/1978 | Farish | H01H 33/22 218/85 |

(Continued)

FOREIGN PATENT DOCUMENTS

| | | |
|---|---|---|
| EP | 1132746 A2 | 9/2001 |
| EP | 1221612 A1 | 7/2002 |
| GB | 555453 A | 8/1943 |

OTHER PUBLICATIONS

Anonymous: "CBWatch-2 Modular Circuit Breaker Monitoring System"; Alstom Product Brochure; Sep. 1, 2010; 4 pages.

(Continued)

*Primary Examiner* — Peter Macchiarolo
*Assistant Examiner* — Nathaniel Kolb
(74) *Attorney, Agent, or Firm* — St. Onge Steward Johnston & Reens LLC

(57) ABSTRACT

A method and device for operating a fluid-insulated electrical apparatus. The insulation fluid of the electrical apparatus includes at least two components. The method includes the step of determining a physical state of the insulation fluid by measuring at least three measurement variables with sensors. The method further includes the step of deriving trend variables indicative of changes over time for the measurement variables and/or for characterizing variables. These characterizing variables are derived from the measurement variables by using a relating equation, such as an equation of state, and are also indicative of the physical state of the insulation fluid. By testing for specific patterns of the trend variables, an operating state of the electrical apparatus is determined. The possible operating states correspond to specific and distinguishable non-fault and fault scenarios for the electrical apparatus. Thus, operating states can be distinguished and troubleshooting in case of a failure is simplified.

43 Claims, 4 Drawing Sheets

(56) References Cited

U.S. PATENT DOCUMENTS

| | | | |
|---|---|---|---|
| 6,272,905 B1* | 8/2001 | Drzewiecki | A61M 16/0051 422/83 |
| 6,305,212 B1 | 10/2001 | Drzewiecki | |
| 7,184,895 B2 | 2/2007 | Chetay et al. | |
| 2002/0095262 A1* | 7/2002 | Chetay | G01N 33/0032 702/24 |
| 2012/0118043 A1* | 5/2012 | Heckler | H01H 33/563 73/30.02 |

OTHER PUBLICATIONS

Hillers, et al.; "Control, Monitoring and Diagnostics for High Voltage GIS"; © 1995 The Institution of Electrical Engineers; pp. 6/1-6/4.

International Preliminary Report on Patentability Application No. PCT/EP2012/075207 Completed: Feb. 25, 2014 11 pages.

International Search Report Application No. PCT/EP2012/075207 Completed: Mar. 25, 2013; Mailing Date: Apr. 4, 2013 3 pages.

T. Löfquist et. al: "Speed of Sound Measurements in Gas-Mixtures at Varying Composition Using an Ultrasonic Gas Flow Meter With Silicon Based Transducers" (e.g. http://pure.ltu.se/portal/files/60931/artikel.pdf as ac-cessed on Nov. 18, 2011.

"Thermodynamic equation describing the state of matter under a given set of physical conditions", from http://en.wikipedia.org/wiki/Equation_of_state as accessed on Nov. 16, 2011; 10 pages.

* cited by examiner

| Fault Scenario | Real change | | | CV | CV | MV | CV | CV | CV | Analysis Conclusion | Operat. state |
|---|---|---|---|---|---|---|---|---|---|---|---|
| | $p^*_A/T$ | $p^*_B/T$ | $p^*_A/p^*_B$ | $p_{tot}/T$ | $\rho_{tot}$ | $p_A/T$ | $p_B/T$ | $p_A/p_B$ | | |
| Uniform Leakage | ↓ | ↓ | ↕ | ↓ | ↓ | ↓ | ↓ | ↕ | Distinguishable against all other fault scenarios and exact determination of $p_A$ and $p_B$ | F1 |
| Preferential leakage | ↓ | ⬇ | ← | ↓ | ↓ | ↓ | ⬇ | ← | | F2 |
| Condensation of component A | ↓ | ↕ | ↓ | ↓ | ↓ | ↓ | ↕ | ↓ | | F3 |
| Appearance of new species C | ↕ | ↕ | ↕ | ↑ | ↑ | ↓ | ← | ↓ | Erroneous values for $p_A$ and $p_B$ but distinguishable | F4 |
| Unimolecular decomposition A → kX (k>1) | ↓ | ↕ | ↓ | ↑ | ↕ | ↓ | ← | ↓ | | F5 |
| | ↕ | ↕ | ↕ | ↕ | ↕ | ↕ | ↕ | ↕ | Operational | O |

MV: measurement variable
CV: characterizing variable

Fig. 2

| Fault Scenario | Real change | | | CV $p_{tot}/T$ | MV $\rho_{tot}$ | CV $p_A/T$ | CV $p_B/T$ | CV $p_A/p_B$ | Analysis Conclusion | Operat. state |
|---|---|---|---|---|---|---|---|---|---|---|
| | $p^*_A/T$ | $p^*_B/T$ | $p^*_A/p^*_B$ | | | | | | | |
| Reaction $mA+nB \rightarrow kX$ ($k>m+n$) | → | → | dep. on $m/n$ | ← | ↕ | → | ← | → | Erroneous values of $p_A$ and $p_B$ but distinguishable | F6 |
| Reaction $mA+nB \rightarrow kX$ ($k<m+n$) | → | → | dep. on $m/n$ | → | ↕ | ← | → | ← | Erroneous values of $p_A$ and $p_B$ but distinguishable | F7 |
| Reaction $mA+nB \rightarrow kX$ ($k=m+n$) | → | → | dep. on $m/n$ | ↕ | ↕ | ↕ | ↕ | ↕ | No fault | F8 |
| Reaction with impurity $mA+jY \rightarrow kX$ ($k>m+j$) | → | ↕ | → | ← | ↕ | → | ← | → | Erroneous values of $p_A$ and $p_B$ but distinguishable | F9 |
| Reaction with impurity $mA+jY \rightarrow kX$ ($k<m+j$) | → | ↕ | → | → | ↕ | ← | → | ← | Erroneous values of $p_A$ and $p_B$ but distinguishable | F10 |
| Reaction with impurity $mA+jY \rightarrow kX$ ($k=m+j$) | → | ↕ | → | ↕ | ↕ | ↕ | ↕ | ↕ | No fault | F11 |

MV: measurement variable
CV: characterizing variable

Fig. 3

| Fault Scenario | Real change | | | CV | MV | CV | CV | CV | Analysis Conclusion | Operat. state |
| --- | --- | --- | --- | --- | --- | --- | --- | --- | --- | --- |
| | $p^*_A/T$ | $p^*_B/T$ | $p^*_A/p^*_B$ | $p_{tot}/T$ | $c_S$ | $p_A/T$ | $p_B/T$ | $p_A/p_B$ | | |
| Uniform leakage | → | → | ↔ | → | ↔ | → | → | ↔ | Distinguishable against all other scenarios and exact determination of $p_A$ and $p_B$ | F12 |
| Preferential leakage | → | ⇒ | ← | → | → | → | ⇒ | ← | | F13 |

MV: measurement variable
CV: characterizing variable

Fig. 4

# METHOD FOR OPERATING AN ELECTRICAL APPARATUS

FIELD OF THE INVENTION

The present invention relates to a method for operating a fluid-insulated electrical apparatus. Furthermore, it relates to such an electrical apparatus having a control and analysis unit implementing such a method.

BACKGROUND OF THE INVENTION

Dielectric insulation media in liquid and/or gaseous states (i.e. fluids) are widely applied to insulate an electrically active part in a variety of electrical apparatuses, such as switchgears or transformers. For example, the electrically active part in medium or high voltage metal-encapsulated switchgear is arranged in a gas-tight compartment which encloses an insulation gas with a pressure of several bars which electrically separates the compartment of the apparatus from the electrically active part. In other words, the insulation gas does not allow the passage of electrical current from the electrically active part to the compartment. A commonly used dielectric insulation gas is sulfur hexafluoride ($SF_6$) which exhibits excellent insulation and electric arc extinguishing capabilities. However, $SF_6$ is a strong contributor to the green-house effect and thus has a high global warming potential. Therefore alternative insulation fluids should be found.

Several alternative insulation fluids have been identified. Some of these alternatives comprise multi-component fluid mixtures, i.e. they comprise more than one molecular or atomic species. It is found that certain properties of such insulation fluid mixtures are viable for the safe operation of the electrical apparatus. As an example, the dielectric breakdown strength of the insulation fluid is strongly dependent on the concentration ratio of the mixture components and on the total fluid pressure. In order to maintain the mixture's insulating features and thus the safety and functionality of the electrical apparatus, the concentrations of the different components of the insulation fluid and the total number of particles in the fluid must remain constant or at least within certain boundaries. For this, sensor devices are used to monitor the physical state of the insulation fluid.

For electrical apparatuses insulated with a single component gas such as $SF_6$, such a monitoring can be achieved by measuring the fluid density inside all gas-filled compartments of the electrical apparatus. Because the density of a gas inside a closed volume is independent of pressure and temperature, a density measurement gives a direct indication of whether, e.g., a leakage fault is present or not. For insulation fluid mixtures, a density measurement alone does not suffice, because the dielectric insulation strength additionally depends, e.g., on the ratio of the components.

US 2002/0095262 A1 and U.S. Pat. No. 7,184,895 B2 describe methods and devices for monitoring the proportion of a component in a gaseous insulation medium consisting of at least two components.

The disclosed methods and devices have the disadvantage, however, that they do not determine and/or distinguish fault scenarios for the insulation media that can compromise the safe operation of the electrical apparatus.

Hillers et al., "Control, monitoring and diagnostics for high voltage GIS", IEE Colloqium on GIS at transmission and distribution voltages (Digest No. 1995/293), 14 Nov. 1995, Nottingham, IEE London (UK) discloses GIS monitoring based on $SF_6$ Gas monitoring, optionally in combination with partial discharge measurement and arc detection.

The Alstom product brochure "CBWatch-2 Modular circuit breaker monitoring system" discloses circuit breaker trend monitoring based on measurement of total gas pressure and gas temperature and subsequent calculation of gas density. As well, liquefaction, $SF_6$ leakage rates, close and open operating times, contacts separation speed, and other circuit breaker and drive variables can be watched.

SUMMARY OF THE INVENTION

Hence it is a general objective of the present invention to provide an improved method for operating an electrical apparatus, wherein a plurality of operating states is distinguished. It is a further object of the invention to provide an electrical apparatus that implements such an operating method. Another object of the invention is to provide a computer program element that implements such a method.

These objectives are achieved by the method and devices of the independent claims.

Accordingly, a method for operating a fluid-insulated electrical apparatus (e.g. gas-insulated medium or high voltage switchgear, a gas-insulated line, or a gas-insulated transformer) comprises the step of determining a physical (e.g. thermodynamic) state of the insulation fluid in the electrical apparatus. The insulation fluid comprises at least two components A and B, i.e. it comprises a mixture of at least a first component A and a second component B. Such components can be liquid and/or gaseous, e.g. component A can be (technical) air and component B can be, e.g., one of the perfluoroketones C5, C6, or C7 (see definitions below). The physical state of the insulation fluid is determined by measuring at least three measurement variables, e.g. a pressure p, a temperature T, and a density $\rho$ of the insulation fluid. This is achieved by means of one or more sensor(s). These measurement variables (e.g. p, T, $\rho$ in the above example) are indicative of the physical state of the insulation fluid. Thus, the physical state of the insulation fluid can be determined from the measurement variables.

The measurement variables are selected such that at least two characterizing variables indicative of partial pressures ($p_A$, $p_B$) or concentrations ($c_A$, $c_B$) of the components (A, B) of the insulation fluid can be determined or are determinable from them. The term "can be determined" herein means that it is possible to determine or calculate the characterizing variables which are indicative of the partial pressures ($p_A$, $p_B$) or concentrations ($c_A$, $c_B$) of the components (A, B) of the insulation fluid from the measurement variables. Thus, a mixing ratio of the components (A, B) is easier to quantify.

For at least one of these measurement variables, at least one trend variable is derived. This trend variable is indicative of a change over time of the at least one measurement variable. For example, the trend variable can be a time derivative of the measurement variable or it can be indicative of an absolute or relative change of the measurement variable over a given temporal interval, i.e. between a first and a second time. Additionally or alternatively to deriving the trend variable for the measurement variable, at least one trend variable for at least one of the characterizing variables is derived which is indicative of a change over time of the at least one of the characterizing variables. The at least one of the characterizing variables is derived from one or more of the measurement variables.

In other words, the trend variable is indicative of a change over time of one or more of the measurement variable(s) and/or of one or more derived variables indicative of partial pressures ($p_A$, $p_B$) or concentrations ($c_A$, $c_B$) of the first component (A) and the second component (B) of the insulation` fluid, which is or are called characterizing variable(s). These characterizing variable(s) is or are also indicative of the physical state of the insulation fluid. With the above mentioned measurement variables example p, T, ρ, possible characterizing variables are, e.g., partial pressures $p_A$ and $p_B$ of the first and second components A and B of the insulation fluid.

The trend variable(s) can, e.g., be derived by comparing a current value or set of values of the respective variable(s) with a running average of the respective variable(s). Thus, a change over time of a measurement variable and/or a characterizing variable is derivable.

According to the invention, at least two trend variables are derived for the at least two characterizing variables (which are indicative of the partial pressures ($p_A$, $p_B$) or concentrations ($c_A$, $c_B$) of the components (A, B) of the insulation fluid). These at least two characterizing variables are selected from the group consisting of
- a function $f1(p_A)$ with $p_A$ being a partial pressure of the first component A of the insulation fluid,
- a function $f2(p_A/T)$ with T being a temperature of the insulation fluid,
- a function $f3(p_B)$ with $p_B$ being a partial pressure of the second component B of the insulation fluid,
- a function $f4(p_B/T)$,
- a function $f5(p_A, p_B)$,
- a function $f6(p_A, p_B, T)$,
- a function $f7(p_A/p_B)$,
- a function $f8(c_A)$ with $c_A$ being a concentration of the first component A of the insulation fluid,
- a function $f9(c_B)$ with $c_B$ being a concentration of the second component B of the insulation fluid,
- a function $f10(c_A, c_B)$, and
- a function $f11(c_A/c_B)$.

Then, an operating state of the electrical apparatus is determined from a plurality of possible operating states by using the at least one trend variable for the at least one of the characterizing variables, and optionally by using the at least one trend variable for the at least one of the measurement variables. Such possible operating states of the electrical apparatus can, e.g., be "operational" and "failure". Thus, the operating state of the electrical apparatus can be determined and further measures can optionally be taken depending on the operating state of the electrical apparatus and optionally on further parameters.

In embodiments, a gaseous phase of the insulation fluid comprises a gaseous mixture of the components of the insulation fluid. Then, at least one of the measurement variables is measured in this gaseous phase of the insulation fluid. This has the advantage that the physical state of the gaseous phase of the insulation fluid is easier to determine.

In other embodiments of the method, at least a first possible operating state of the electrical apparatus corresponds to at least a first non-fault scenario for the electrical apparatus. At least a second possible operating state of the electrical apparatus corresponds to at least a first fault scenario for the electrical apparatus. Furthermore, the physical state of the insulation fluid (as, e.g., determined from the measurement variables and/or from the characterizing variable(s)) in the first possible operating state (corresponding to the first non-fault scenario) is different from the physical state of the insulation fluid (as, e.g., determined from the measurement variables and/or from the characterizing variable(s)) in the second possible operating state (corresponding to the first fault scenario). Alternatively or additionally, the trend variable(s) is or are different in the first and second possible operating states. This has the advantage that the first possible operating state of the electrical apparatus (which corresponds to the first non-fault scenario) can be distinguished from the second possible operating state of the electrical apparatus (which corresponds to the first fault scenario).

Thus, trouble-shooting is simplified. In embodiments, at least a third possible operating state of the electrical apparatus corresponds to at least a second fault scenario for the electrical apparatus. Furthermore, the physical states of the insulation fluid of the electrical apparatus and the trend variable(s) differ in the first possible operating state of the electrical apparatus (corresponding to the first non-fault scenario), in the second possible operating state of the electrical apparatus (corresponding to the first fault scenario), and in the third possible operating state of the electrical apparatus (corresponding to the second fault scenario). This has the advantage that the first, the second, and the third possible operating states of the electrical apparatus can be distinguished using the at least one trend variable. Thus, distinguishing of fault scenarios and trouble-shooting are simplified.

In embodiments, the first and second fault scenarios for the electrical apparatus (corresponding to the second and third possible operating state of the electrical apparatus, respectively) are selected from the group consisting of:
- uniform leakage of the insulation fluid, i.e. component-independent loss of insulation fluid from a compartment of the electrical apparatus,
- preferential leakage of one component (A or B) of the insulation fluid, i.e. increased loss of one component compared to the other component, thus leading to a change of a mixing ratio of the insulation fluid,
- condensation or preferred condensation of one component of the insulation fluid, e.g. a state transition from gaseous to liquid state or vice versa of only one or at least preferably one component (A or B) of the insulation fluid,
- appearance of at least one new component (C) in the insulation fluid, e.g. due to arcing, partial discharges, light, high temperature, and/or reactions of at least one of the components (A and/or B) with materials in the electrical apparatus,
- decomposition or preferred decomposition of at least one component (A and/or B) of the insulation fluid, e.g. due to arcing, partial discharges, light, high temperature, and/or reactions of at least one of the components (A and/or B) with materials in the electrical apparatus,
- intermolecular reactions between molecules of the at least two components (A, B) of the insulation fluid, and
- removal of at least one of the at least two components (A, B) of the insulation fluid, e.g. due to adsorption onto surfaces.

Thus, a plurality of different fault scenarios for the electrical apparatus can be distinguished.

For example, measurement variables can at least be indicative of a pressure (p) and a temperature (T) of the insulation fluid. Thus, a determination of the physical state of the insulation fluid is simplified.

In embodiments, the measurement variables can at least be indicative of the pressure (p), the temperature (T), and a density (ρ) of the insulation fluid. Thus, a determination of the physical state of the insulation fluid is simplified.

Other exemplary measurement variables can additionally be indicative of at least one element of the group consisting of a thermal conductivity (λ), a viscosity (η), and a speed of sound ($c_S$) of or in the insulation fluid. Thus, a determination of the physical state of the insulation fluid is simplified.

In other embodiments, at least one characterizing variable indicative of the respective partial pressure ($p_A$, $p_B$) or concentration ($c_A$, $c_B$) is derived for each component of the insulation fluid. Preferably at least said two of said characterizing variables indicative of the partial pressures ($p_A$, $p_B$) or concentrations ($c_A$, $c_B$) are derived for both components (A, B) of the insulation fluid. At least one relating equation is used for deriving the characterizing variable(s) from the measurement variables. In other words, by using the relating equation, the characterizing variable which is indicative of the partial pressure ($p_A$, $p_B$) or concentration ($c_A$, $c_B$) of the component (A or B) of the insulation fluid is derived from the measurement variables, or by using the relating equation (s), the characterizing variables which are indicative of the partial pressures ($p_A$, $p_B$) or concentrations ($c_A$, $c_B$) of the components (A, B) of the insulation fluid is derived from the measurement variables. This relating equation can be the same (i.e. the same relating equation is used for both components) or different (i.e. different relating equations are used for both components) for each of the components (A, B) of the insulation fluid. Thus, a suitable relating equation can be used for each component.

In other embodiments, the measurement variables are at least indicative of the pressure (p), the temperature (T), and the density ($\rho$) of the insulation fluid. Then, at least one of the relating equations can be an equation of state (i.e. a "thermodynamic equation describing the state of matter under a given set of physical conditions" (from http://en.wikipedia.org/wiki/Equation_of_state as accessed on Nov. 16, 2011)) which is selected from the group consisting of:

the ideal gas law, i.e. pV=nRT with p being an absolute pressure, V being a volume, n being a number of molecules (usually expressed in moles), R being the ideal gas constant, and T being an absolute temperature, the van-der-Waals equation of state, i.e. $(p+a/V_m^2)(V_m-b)=RT$ with $V_m$ being a molar volume and a, b being substance-specific parameters for the respective component (in particular, a and b can also be derived as effective parameters for a specific insulation fluid mixture), the virial equation of state, i.e. $pV_m/(RT)=1+B(T)/V_m+C(T)/V_m^2+D(T)/V_m^3+\ldots$ with B(T), C(T), D(T), ... being temperature-dependent terms that correspond to interactions between molecules, the Beattie-Bridgeman equation of state, i.e. $p=R_uT/(v^2)(1-c/(vT^3))(v+B)-A/(v^2)$ with $A=A_0(1-a/v)$, $B=B_0(1-b/v)$, $R_u$ being a gas constant in the form $R_u$=8.314 kPa m$^3$/(kmol K), v being a molar volume, and a, b, c, $A_0$, and $B_0$ being substance-specific parameters for the respective component (in particular, again the parameters can also be derived as effective parameters for a specific insulation fluid mixture), and the Peng-Robinson equation of state, i.e. $p=RT/(V_m-b)-a(T)/(V_m(V_m+b)+b(V_m-b))$ with a(T) and b being empirical parameters.

When an equation of state other than the ideal gas law is used, the behavior of a gas can be better predicted than with the ideal gas law alone and the prediction can be extended to liquids. This is possible by putting in terms to describe attractions and repulsions between molecules.

In embodiments, the partial pressures or concentrations of the first component (A) and of the second component (B) of the insulation fluid differ at least by a factor of 2, i.e. the partial pressure ($p_A$) or concentration ($c_A$) of the first component (A) is at least by a factor of 2 higher than the partial pressure(s) or concentration(s) of the other components of the insulation fluid. Then, one (i.e. the same) relating equation is used for deriving the characterizing variables (which are indicative of the partial pressures ($p_A$, $p_B$) or concentrations ($c_A$, $c_B$) of the components (A, B) of the insulation fluid) using the measurement variables. This simplifies the derivation of the characterizing variables from the measurement variables.

All mentioned functions f1 . . . f11 can depend on additional variables. Preferably, the functions f1 . . . f11 are monotonous functions of their variables.

Thus, the at least two trend variables reflect the change over time of partial-pressure or concentration dependent functions for the respective components of the insulation medium.

In another embodiment of the method, trend variables are derived at least for measurement variables or characterizing variables indicative of p/T,
$p_A$/T or $c_A$,
$p_B$/T or $c_B$, and
$p_A/p_B$ or $c_A/c_B$ of the insulation fluid (with p being the pressure and T being the temperature of the insulation fluid and $p_A$, $p_B$, $c_A$, and $c_B$ being partial pressures and concentrations of the components of the insulation fluid). In other words, these trend variables are indicative of a change over time of p/T,
$p_A$/T or $c_A$,
$p_B$/T or $c_B$, and
$p_A/p_B$ or $c_A/c_B$.

Thus, the change over time of these measurement variables and characterizing variables can be determined.

In another embodiment, a further trend variable is derived for a or the measurement variable indicative of $\rho$ (with $\rho$ being the density of the insulation fluid). The method further comprises the method element of testing for a specific pattern or for specific patterns of these trend variables (see below). Thus, a plurality of operating states can be distinguished.

In another embodiment of the method, the second component is selected from the group consisting of:

sulfur hexafluoride, partially or fully fluorinated ethers, in particular hydrofluoroethers, hydrofluoro monoethers, hydrofluoro monoethers containing at least 3 carbon atoms, perfluoro monoethers, or perfluoro monoethers containing at least 4 carbon atoms, partially or fully fluorinated ketones, in particular hydrofluoro monoketones, perfluoro monoketones, perfluoro monoketones comprising at least 5 carbon atoms, or perfluoro monoketones comprising exactly 5 or 6 or 7 or 8 carbon atoms, and mixtures thereof.

The first component is selected from the group consisting of:

nitrogen,
oxygen,
carbon dioxide,
nitric oxide,
nitrogen dioxide,
nitrous oxide,
argon,
methanes, in particular partially or fully halogenated methanes, in particular tetrafluoromethane or trifluoroiodomethane,
air, in particular technical air or synthetic air, and
mixtures thereof.

Thus, an improved insulation performance can be achieved for the insulation fluid of the electrical apparatus.

In embodiments, the second component is selected from the group consisting of:

cyclic and/or aliphatic fluoropentanones, preferably cyclic and/or aliphatic perfluoropentanones, more preferably 1,1,1,3,4,4,4-heptafluoro-3-(tri-fluoromethyl)butan-2-one, cyclic and/or aliphatic fluorohexanones, preferably cyclic and/or aliphatic perfluorohexanones, more preferably 1,1,1,2,4,4,5,5,5-nonafluoro-4-(trifluoromethyl)pentan-3-one, cyclic and/or aliphatic fluoroheptanones, preferably cyclic and/or aliphatic perfluoroheptanones, sulfur hexafluoride, and hydrofluoroethers.

Thus, an improved insulation performance can be achieved for the insulation fluid of the electrical apparatus.

In other embodiments, the first component consists of:

nitrogen and oxygen with relative partial pressures between $p(N_2)/(p(O_2)+p(N_2))=0.7$, $p(O_2)/(p(O_2)+p(N_2))=0.3$ and $p(N_2)/(p(O_2)+p(N_2))=0.95$, $p(O_2)/(p(O_2)+p(N_2))=0.05$, or carbon dioxide and oxygen with relative partial pressures between $p(CO_2)/(p(CO_2)+p(CO_2))=0.6$, $p(O_2)/(p(O_2)+p(CO_2))=0.4$ and $p(CO_2)/(p(O_2)+p(CO_2))=0.99$, $p(O_2)/(p(O_2)+p(CO_2))=0.01$, or carbon dioxide and nitrogen with relative partial pressures between $p(CO_2)/(p(N_2)+p(CO_2))=0.1$, $p(N_2)/(p(N_2)+p(CO_2))=0.9$ and $p(CO_2)/(p(N_2)+p(CO_2))=0.9$, $p(N_2)/(p(N_2)+p(CO_2))=0.1$.

The second component comprises at least one of the group consisting of:

1,1,1,3,4,4,4-heptafluoro-3-(tri-fluoromethyl)butan-2-one with a partial pressure between 0.1 bar and 0.7 bar at a temperature of 20° C., 1,1,1,2,4,4,5,5,5-nonafluoro-4-(trifluoromethyl)pentan-3-one with a partial pressure between 0.01 bar and 0.3 bar at a temperature of 20° C., sulfur hexafluoride with a partial pressure between 0.1 bar and 2 bar at a temperature of 20° C., and hydrofluoroethers with a partial pressure between 0.2 bar and 1 bar at a temperature of 20° C.

Thus, an improved insulation performance can be achieved for the insulation fluid of the electrical apparatus.

In other embodiments, the first component comprises nitrogen and oxygen with relative partial pressures between $p(N_2)/(p(O_2)+p(N_2))=0.75$, $p(O_2)/(p(O_2)+p(N_2))=0.25$ and $p(N_2)/(p(O_2)+p(N_2))=0.90$, $p(O_2)/(p(O_2)+p(N_2))=0.10$, and wherein the second component comprises 1,1,1,3,4,4,4-heptafluoro-3-(tri-fluoromethyl)bu-tan-2-one with a partial pressure between 0.25 bar and 0.5 bar and/or 1,1,1,2,4,4,5,5,5-nona-fluoro-4-(tri-fluoromethyl)pentan-3-one with a partial pressure between 0.02 bar and 0.3 bar at a temperature of 20° C.

Thus, an improved insulation performance can be achieved for the insulation fluid of the electrical apparatus.

In other embodiments, the method further comprises the step or element of issuing a signal (e.g. issuing a warning signal to an operator and/or issuing a machine-readable, e.g. computer-readable, signal) when the electrical apparatus enters or leaves a possible operating state. More advantageously, this signal is an alert signal that is, e.g., issued when the electrical apparatus leaves the "operational" possible operating state. More advantageously, the method further comprises the method element of shutting down the electrical apparatus, when, e.g., the operating state of the electrical apparatus changes from "operational" to "failure". Thus, a safe operation of the electrical apparatus can be maintained.

In other embodiments, the method further comprises a method element of actively or passively circulating the insulation fluid for homogenizing a density and/or a mixture of the first and/or the second components, e.g. by means of a fan or by convection. This step or method element is preferably carried out before the step or method element of measuring the at least three measurement variables. Thus, the measurement variables can be measured in a more meaningful way.

In other embodiments, the method further comprises at least one step or method element of the group consisting of:

Increasing at least one partial pressure or at least one concentration of the first and/or of the second component of the insulation fluid. This can, e.g., be achieved by means of injecting an amount of the first and/or of the second component from a component reservoir into the compartment of the electrical apparatus. Thus, the first and/or the second component of the insulation fluid in the compartment can be replenished on demand which minimizes downtime of the electrical apparatus in case of a malfunction.

Reducing at least one partial pressure or at least one concentration of the first and/or of the second component of the insulation fluid. Thus, an excess amount of one or both component(s) of the insulation fluid can be removed from the compartment of the electrical apparatus.

Reducing a concentration of at least one contaminant (i.e. an unwanted substance in the insulation fluid) in the insulation fluid, in particular by means of a filter adsorbing the contaminant. Thus, unwanted substances which can lower the insulation performance can be removed from the insulation fluid.

At least partially evaporating a condensed amount of at least the first and/or of the second component of the insulation fluid. This can, e.g., be achieved by means of a heater located in the lower part of the compartment. Thus, unwanted insulation-fluid-condensation which can occur, e.g., at low ambient temperatures, can be effectively counteracted.

Condensing an amount of the first and/or of the second component of the insulation fluid, in particular by means of a cooler. Thus, the gaseous amount of the condensed component can be reduced.

As a consequence of carrying out one or more of the above steps or method elements, a suitable mixing ratio for the insulation fluid can be more easily maintained. This or these step(s) are preferably selected in dependence of or using the operating state in which the electrical apparatus is in.

As another aspect of the invention, a fluid-insulated electrical apparatus (e.g. medium or high voltage gas-isolated switchgear) comprises an insulation fluid which comprises at least two components (A, B). Furthermore, the electrical apparatus comprises at least one sensor for measuring at least three measurement variables which are indicative of a physical (e.g. thermodynamic) state of the insulation fluid. The electrical apparatus furthermore comprises a control and analysis unit which is adapted to carry out the steps or method elements of a method for operating the fluid-insulated electrical apparatus as described above. Thus, the electrical apparatus can be operated and, e.g., its safe operation can be maintained.

In embodiments, the control and analysis unit is adapted to issue a signal (e.g. to issue a warning or an alert signal) when the electrical apparatus enters or leaves a possible operating state. In other embodiments, the control and analysis unit is adapted to shutdown the electrical apparatus, e.g. when the operating state of the electrical apparatus changes from "operational" to "failure". Thus, a safe operation of the electrical apparatus can be maintained.

In other embodiments, the control and analysis unit of the electrical apparatus is furthermore adapted to distinguish at least a first, a second, and a third operating state of a plurality of possible operating states (O, F1, F2) of the electrical apparatus. At least the second and the third operating states correspond to a first and second fault scenario for the electrical apparatus, respectively. This has the advantage that the first possible operating state of the electrical apparatus (which corresponds to the first non-fault scenario) can be distinguished from the second possible operating state of the electrical apparatus (which corresponds to the first fault scenario) and from the third possible operating state of the electrical apparatus (which corresponds to the second fault scenario). Thus, trouble-shooting in case of a failure of the electrical apparatus is simplified or enabled.

As another aspect of the invention, a computer program element comprising computer program code means for, when executed by a processing unit, implementing a method as described above is disclosed. This enables the integration of a method as described above into an electrical apparatus comprising a control and analysis unit.

BRIEF DESCRIPTION OF THE DRAWINGS

The invention and its embodiments will be more fully appreciated by reference to the following detailed description of presently preferred but nonetheless illustrative embodiments in accordance with the present invention when taken in conjunction with the accompanying drawings.

FIGS. 2, 3, and 4 show real changes as well as a response of the trend variables for a plurality of possible operating states of an electrical apparatus. Furthermore, an analysis conclusion is shown.

DETAILED DESCRIPTION OF THE INVENTION

Figure 1:
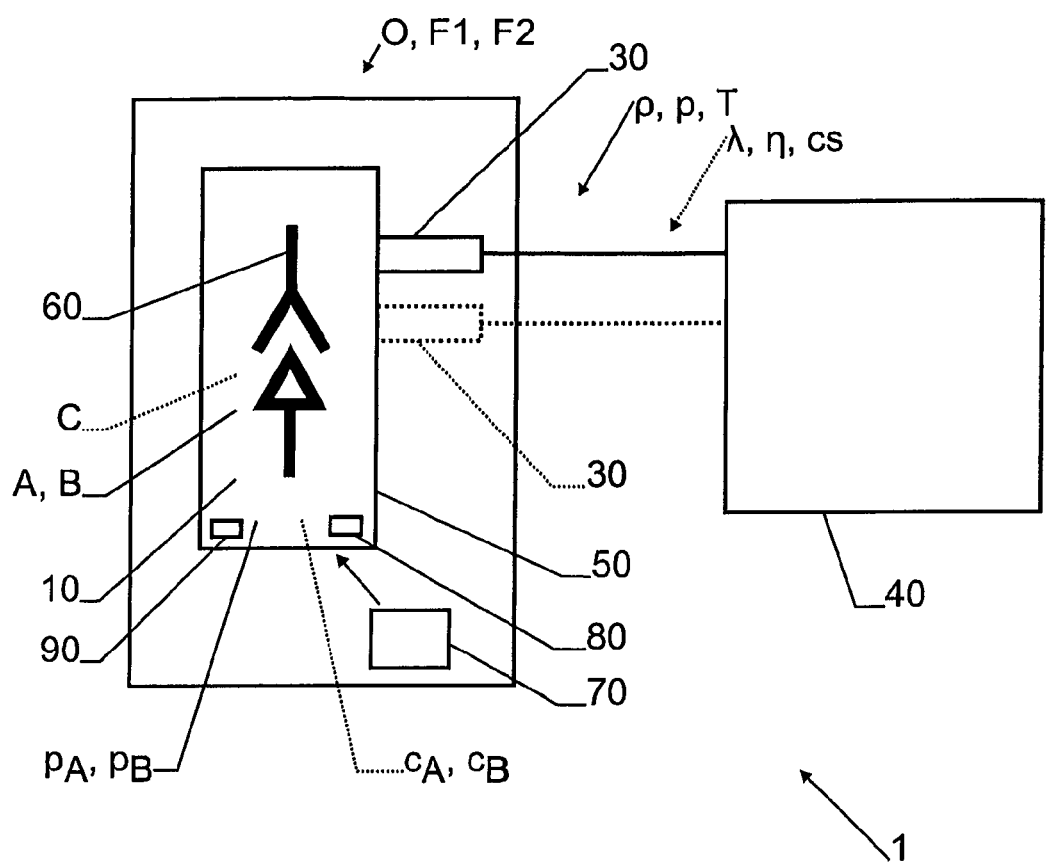
FIG. 1 shows a schematic of a fluid-insulated electrical apparatus.

FIG. 1 shows a schematic of a fluid-insulated electrical apparatus 1, i.e. here, e.g., a gas insulated switch 1. An electrically active part 60 of the fluid-insulated switch 1 is arranged in a gas-tight compartment 50 which encloses an insulation fluid 10 for preventing the passage of electrical current from the electrically active part 60 to the compartment 50. The insulation fluid 10 is an insulation gas 10 comprising, e.g., a first component A "technical air" (i.e. a gas mixture of oxygen with a mole fraction of 0.2 and of nitrogen with a mole fraction of 0.8) and a second component B "perfluoroketone C5" (see definition below) with a mixing ratio of 95:5 at filling time and a total filling pressure of p=7 bar. This mixing ratio corresponds to partial pressures $p_A$=6.7 bar and $p_B$=0.35 bar or concentrations in mole fractions $c_A$=0.95 and $c_B$=0.05 for components A and B, respectively. Additionally or as replacement for component B, a component "perfluoroketone C6" or "perfluoroketone C7" (component C, dotted) with a partial pressure $p_{C,C6}$=0.1 bar ($c_{C,C6}$=0.014) and $p_{C,C7}$=0.05 bar ($c_{C,C7}$=0.007) can be added to the insulation gas 10.

The physical state (as determinable using suitable measurement variables) of the insulation gas 10 is determined by a control and analysis unit 40 by measuring three measurement variables in a gaseous phase of the insulation gas 10 by means of a sensor 30. Here, the physical state of the insulation gas 10 is determined using the total pressure p, the temperature T, and the density ρ of the insulation gas 10. E.g., WO 2010/043268 A1 discloses a suitable density sensor device for this purpose.

As an option, additionally or as a replacement for the density ρ of the insulation gas 10, other suitable measurement variables like thermal conductivity λ, viscosity η, and/or speed of sound $c_S$ of/in the insulation gas 10 can be measured by the same or a different sensor device 30 (dotted). The measurement variables can then be related to the concentration values $c_A$, $c_B$ of the components A and B of the insulation fluid 10, e.g. by using the following relating equations (if pressure p, temperature T, and speed of sound $c_S$ are measured):

$$c_S = \sqrt{\frac{RT(c_A c_{pA} + c_B c_{pB})}{(c_A M_A + c_B M_B)(c_A c_{VA} + c_B c_{VB})}}$$

with $c_A$ and $c_B$ being the desired concentration values in mole fractions of the components A and B with $c_A+c_B=1$, $c_A=p_A/p$, and $c_B=p_B/p$, $p_A$ and $p_B$ being partial pressures of the components A and B, R being the ideal gas constant, $M_A$ and $M_B$ being (averaged) molecular masses of the components A and B, and $c_{pA}$, $c_{pB}$, $c_{VA}$, and $c_{VB}$ being known specific heat values of the components A and B at constant pressures and constant volumes, respectively.

If pressure p, temperature T, and viscosity η are measured, the following relating equation can, e.g., be used:

$$\eta(T) = \frac{c_A \eta_A(T)}{c_A \Phi_{AA} + c_B \Phi_{AB}} + \frac{c_B \eta_B(T)}{c_B \Phi_{BB} + c_A \Phi_{BA}} \text{ with}$$

$$\Phi_{ij}(T) = \frac{1}{2\sqrt{2}}\left(1 + \frac{M_i}{M_j}\right)^{-1/2}\left[1 + \left(\frac{\eta_i(T)}{\eta_j(T)}\right)^{1/2}\left(\frac{M_j}{M_i}\right)^{1/4}\right]^2$$

and with $c_A$ and $c_B$ being the desired concentration values in mole fractions of the components A and B with $c_A+c_B=1$, $c_A=p_A/p$, and $c_B=p_B/p$, $p_A$ and $p_B$ being partial pressures of the components A and B, $\eta_A(T)$ and $\eta_B(T)$ being known temperature dependent viscosities of the components A and B, and $M_A$ and $M_B$ being (averaged) molecular masses of the components A and B.

If pressure p, temperature T, and thermal conductivity λ are measured, the following relating equation can, e.g., be used:

$$\lambda(T) = \frac{c_A \lambda_A(T)}{c_A \Phi_{AA} + c_B \Phi_{AB}} + \frac{c_B \lambda_B(T)}{c_B \Phi_{BB} + c_A \Phi_{BA}} \text{ with}$$

$$\Phi_{ij}(T) = \frac{1}{2\sqrt{2}}\left(1 + \frac{M_i}{M_j}\right)^{-1/2}\left[1 + \left(\frac{\eta_i(T)}{\eta_j(T)}\right)^{1/2}\left(\frac{M_j}{M_i}\right)^{1/4}\right]^2$$

and with $c_A$ and $c_B$ being the desired concentration values in mole fractions of the components A and B with $c_A+c_B=1$, $c_A=p_A/p$, and $c_B=p_B/p$, $p_A$ and $p_B$ being partial pressures of the components A and B, $\lambda_A(T)$ and $\lambda_B(T)$ being known temperature dependent thermal conductivities of the components A and B, $\eta_A(T)$ and $\eta_B(T)$ being known temperature dependent viscosities of the components A and B, and $M_A$ and $M_B$ being (averaged) molecular masses of the components A and B.

E.g., U.S. Pat. No. 6,305,212 B1, U.S. Pat. No. 6,272,905 B1, and T. Löfquist et. al: "SPEED OF SOUND MEASUREMENTS IN GAS-MIXTURES AT VARYING COMPOSITION USING AN ULTRASONIC GAS FLOW METER WITH SILICON BASED TRANSDUCERS" (e.g. http:// pure.ltu.se/portal/files/60931/artikel.pdf as accessed on 18 Nov. 2011) give further examples on how to relate different sets of measurement variables.

In this embodiment, this is not necessary, however, because measurement variables indicative of the pressure p, the temperature T, and the density ρ are measured as discussed above. Specifically, signals indicative of these measurement variables are transmitted from the sensors 30 to the control and analysis unit 40, which converts these signals into the measurement variables pressure p, temperature T and density ρ readings and thus determines the physical state of the insulation fluid 10. Then, characterizing variables indicative of the partial pressures $p_A$ and $p_B$ of the components A and B of the insulation fluid 10 are derived from the measurement variables p, T, ρ with the following equations:

$$p_{tot} = p_A + p_B \qquad \text{Eq. 1}$$

$$\rho_{tot} = \frac{M_A p_A}{RT} + \frac{M_B p_B}{RT} \qquad \text{Eq. 2}$$

$$p_A = \frac{\frac{RT}{M_A}\rho_{tot} - \frac{M_B}{M_A}p_{tot}}{\left(1 - \frac{M_B}{M_A}\right)} \qquad \text{Eq. 3}$$

$$p_B = \frac{p_{tot} - \frac{RT}{M_A}\rho_{tot}}{\left(1 - \frac{M_B}{M_A}\right)} \qquad \text{Eq. 4}$$

with $p_{tot}$ being the pressure p, $\rho_{tot}$ being the density ρ, T being the temperature, R being the ideal gas constant, and $M_A$ and $M_B$ being the (averaged) molecular masses of the components A and B, respectively. The average molecular mass $M_A$ for component A is calculated as a weighted average value: $M_A = c(O_2)*M(O_2) + c(N_2)*M(N_2) = 0.2*32$ g/mol + 0.8*28 g/mol = 28.8 g/mol.

Here, the ideal gas law (i.e. an equation of state) pV=nRT and the equations n=m/M and m=ρV with m being a mass and V being a volume are used for both components A and B as an approximation. This is possible, because $p_A$ is by a factor of 19 higher than $p_B$. To improve accuracy, in particular for insulation fluid mixtures containing first and/or second components A and/or B other than noble gases and small di- or triatomic gases, different relating equations or equations of state, such as the van-der-Waals equation of state, should be used for components A and B as discussed above.

Then, the resulting partial pressures $p_A$ and $p_B$ are normalized by dividing $p_A$ and $p_B$ by the temperature T. Thus, characterizing variables indicative of $p_A/T$ and $p_B/T$ are obtained. Further characterizing variables are calculated as p/T and $p_A/p_B$. The control and analysis unit 40 then derives trend variables for p/T, ρ, $p_A/T$, $p_B/T$, and $p_A/p_B$ from the measurement variable indicative of ρ and from the characterizing variables indicative of p/T, $p_A/T$, $p_B/T$, and $p_A/p_B$. For this, temporal averaging algorithms (e.g. running averages or arithmetic averages over predefined time periods, e.g. 1 hour or 1 day or 1 year or 10 years) are used to smoothen the data stream. The trend variables for p/T, ρ, $p_A/T$, $p_B/T$, and $p_A/p_B$ are indicative of a change over time of the measurement variable indicative of ρ and of the characterizing variables indicative of p/T, $p_A/T$, $p_B/T$, and $p_A/p_B$, respectively.

As a next step, the control and analysis unit 40 determines an operating state P or F1 or F2 or F3 or F4 or F5 of the electrical apparatus 1 from the trend variables as it is described below for FIG. 2. This is done by testing for specific patterns of the trend variables. The group of possible operating states comprises [O, F1, F2, F3, F4, F5]. Further possible operating states are also possible (see below). The operating state O of the electrical apparatus 1 corresponds to an "operational" or "non-fault" scenario for the electrical apparatus 1, whereas the operating states F1 to F5 correspond to different "fault" scenarios for the electrical apparatus 1. The physical states of the insulation fluid 10 and/or the trend variables are different in all operating states (see below).

Whenever the electrical apparatus 1 leaves the "operational" operating state, a warning is issued to a user from the control and analysis unit 40 and—depending on the entered operating state and further parameters as, e.g., leakage rate—an emergency shutdown of the electrical switch 1 is initiated.

Optionally, depending on the entered operating state, countermeasures can be taken automatically: As an example, if the ambient temperature drops severely and the second component partly condenses in the lower part of the compartment 50, heater 80 can be ignited to evaporate at least a part of the condensed component, thus ensuring a sufficient gaseous amount.

As another example, if preferential leakage of the first component occurs, e.g. due to a very small leak in the compartment, an amount of the first component can be replenished from a pressurized component reservoir 70, thus minimizing downtime.

As yet another example, a filter 90 can be used to remove an unwanted substance (i.e. a contaminant, e.g. due to arcing) from the insulation fluid.

FIG. 2 shows real changes (marked with an asterisk *) as well as a response of the trend variables for p/T=$p_{tot}$/T, ρ=$\rho_{tot}$, $p_A/T$, $p_B/T$, and $p_A/p_B$ (i.e. a change over time of the respective characterizing and/or measurement variable(s)) as well as an analysis conclusion for a plurality of possible operating states O, F1-F5 of the gas-insulated electrical switch 1.

In the "operational" operating state "O" of the electrical switch 1, p/T, ρ, $p_A/T$, $p_B/T$ and $p_A/p_B$ remain constant, i.e. the respective trend variables are equal to 0. This is shown with a symbol "⇆". In this operating state, the non-fault scenario is detected for the electrical switch 1 and the true values of the characterizing variables $p_A/T$ and $p_B/T$ can be determined from the measurement variables p, ρ, and T.

In the "F1" operating state of the electrical switch 1, p/T, ρ, $p_A/T$, and $p_B/T$ decrease (the respective trend variables are <0, symbol "↓") whereas $p_A/p_B$ remains constant (symbol "⇆"). This leads to the analysis conclusion "fault scenario: uniform leakage for the electrical switch 1", which is a fault scenario which can be distinguished from all other mentioned fault scenarios and in which the true values of the characterizing variables $p_A/T$ and $p_B/T$ can be determined from the measurement variables p, ρ, and T. Depending on the leakage rate, an emergency shutdown of the electrical switch can be initiated when the electrical switch 1 enters the operating state "F1" and/or an operator can be warned, e.g. also including a time-to-react estimation, i.e. a time-estimate in which the electrical switch is about to enter an unsafe state due to a sub-threshold insulation gas pressure (at the current leakage rate).

In the "F2" operating state of the electrical switch 1, p/T, ρ, $p_A/T$, and $p_B/T$ decrease (symbol "↓"). While p/T, ρ, and $p_A/T$ decrease at specific rates, $p_B/T$ decreases at a higher rate than $p_A/T$ (large symbol "↓") and $p_A/p_B$ increases (the respective trend variable is >0, symbol "↑"). This leads to the analysis conclusion "fault scenario: preferential leakage of component B for the electrical switch 1", which is a fault scenario which can be distinguished from all other mentioned fault scenarios and in which the true values of the characterizing variables $p_A/T$ and $p_B/T$ can be determined from the measurement variables p, ρ, and T.

In the "F3" operating state of the electrical switch 1, p/T, ρ, and $p_A/T$ decrease (symbol "↓"), $p_B/T$ remains constant (symbol "↔") and $p_A/p_B$ decreases (symbol "↓"). This leads to the analysis conclusion "fault scenario: condensation of component A for the electrical switch 1", which is a fault scenario which can be distinguished from all other mentioned fault scenarios and in which the true values of the characterizing variables $p_A/T$ and $p_B/T$ can be determined from the measurement variables p, μ, and T.

In the "F4" operating state of the electrical switch 1, p/T, ρ, and $p_B/T$ increase (symbol "↑") and $p_A/T$ and $p_A/p_B$ decrease (symbol "↓"). This leads to the analysis conclusion "fault scenario: appearance of new species for the electrical switch 1", which is a fault scenario which can be distinguished from all other mentioned fault scenarios and in which the true values of the characterizing variables $p_A/T$ and $p_B/T$ cannot be determined from the measurement variables p, ρ, and T.

In the "F5" operating state of the electrical switch 1, p/T and $p_B/T$ increase (symbol "↑"), $p_A/T$ and $p_A/p_B$ decrease (symbol "↓") and ρ remains constant (symbol "↔"). This can (see below) lead to the analysis conclusion "fault scenario: unimolecular decomposition A→kX for the electrical switch 1" (with A being a molecule of component A, k being a natural number with k>1, and X being a molecule of a new component X). This is a fault scenario which can be distinguished from most of the other mentioned fault scenarios (see below). Here, the true values of the characterizing variables $p_A/T$ and $p_B/T$ cannot be determined from the measurement variables p, ρ, and T.

In summary, a plurality of specific patterns of the trend variables are thus unambiguously related to a plurality of specific operating states/fault scenarios for the electrical apparatus 1. This simplifies trouble-shooting in the case of failure.

As it is shown in FIG. 3, a response of the trend variables for $p/T=p_{tot}/T$, $ρ=ρ_{tot}$, $p_A/T$, $p_B/T$, and $p_A/p_B$ (i.e. a change over time of the respective characterizing and/or measurement variables) can also be used to optionally distinguish at least some of a plurality of further possible operating states F6-F11 which are regarded as less usual than the possible operation states O, and F1-F5 described with regard to FIG. 1. Real changes (marked with an asterisk *) as well as analysis conclusions are furthermore shown.

In the "F6" and "F9" operating states of the electrical switch 1, p/T and $p_B/T$ increase (symbol "↑"), $p_A/T$ and $p_A/p_B$ decrease (symbol "↓") and ρ remains constant (symbol "↔"). This can lead to the analysis conclusions "fault scenario: reaction mA+nB→kX for the electrical switch 1" (with A being a molecule of component A, B being a molecule of component B, m, n, and k being natural numbers with k>m+n, and X being a molecule of a new component X) or "fault scenario: reaction with impurity mA+jY→kX for the electrical switch 1" (with A being a molecule of component A, Y being a molecule of an impurity Y, m, j, and k being natural numbers with k>m+j, and X being a molecule of a new component X). These fault scenarios can be distinguished from most of the other mentioned fault scenarios (except—unless further information is gathered—from each other and from F5, see above under "unimolecular decomposition"). The true values of the characterizing variables $p_A/T$ and $p_B/T$ cannot be determined from the measurement variables p, ρ, and T in this case.

In the "F8" and "F11" operating states of the electrical switch 1, p/T, ρ, $p_A/T$, $p_B/T$, and $p_A/p_B$ all remain constant (symbol "↔"). This leads to the erroneous analysis conclusions "operational" (see above), while in reality "fault scenario: reaction mA+nB→kX for the electrical switch 1" (with A being a molecule of component A, B being a molecule of component B, m, n, and k being natural numbers with k=m+n, and X being a molecule of a new component X) or "fault scenario: reaction with impurity mA+jY→kX for the electrical switch 1" (with A being a molecule of component A, Y being a molecule of an impurity Y, m, j, and k being natural numbers with k=m+j, and X being a molecule of a new component X) should be detected. Without further information, these fault scenarios cannot be distinguished from the "non-fault" scenario associated with the "O" operating state (see above).

In the "F7" and "F10" operating states of the electrical switch 1, p/T and $p_B/T$ decrease (symbol "↓"), $p_A/T$ and $p_A/p_B$ increase (symbol "↑") and ρ remains constant (symbol "↔"). This leads to the analysis conclusions "fault scenario: reaction mA+nB→kX for the electrical switch 1" (with A being a molecule of component A, B being a molecule of component B, m, n, and k being natural numbers with k<m+n, and X being a molecule of a new component X) or "fault scenario: reaction with impurity mA+jY→kX for the electrical switch 1" (with A being a molecule of component A, Y being a molecule of an impurity Y, m, j, and k being natural numbers with k<m+j, and X being a molecule of a new component X). Without gathering further information, these fault scenarios can be distinguished from most of the other mentioned fault scenarios (except from each other). The true values of the characterizing variables $p_A/T$ and $p_B/T$ cannot be determined from the measurement variables p, ρ, and T in this case.

FIG. 4 shows real changes (marked with an asterisk *) as well as a response of the trend variables for $p/T=p_{tot}/T$, $c_S$, $p_A/T$, $p_B/T$, and $p_A/p_B$ (i.e. a change over time of the respective characterizing and/or measurement variable(s)) as well as an analysis conclusion for a plurality of possible further operating states F12 and F13.

In the "F12" operating state of the electrical switch 1, p/T, $p_A/T$, and $p_B/T$ decrease (symbol "↓") and $c_S$ and $p_A/p_B$ remain constant (symbol "↔,"). This leads to the analysis conclusion "fault scenario: uniform leakage for the electrical switch 1", which is a fault scenario which can be distinguished from all other mentioned fault scenarios and in which the true values of the characterizing variables $p_A/T$ and $p_B/T$ can be determined from the measurement variables p, $c_S$, and T. Depending on the leakage rate, an emergency shutdown of the electrical switch can be initiated when the electrical switch 1 enters the operating state "F12" and/or an operator can be warned, e.g. also including a time-to-react estimation, i.e. a time-estimate in which the electrical switch is about to enter an unsafe state due to a sub-threshold insulation gas pressure (at the current leakage rate). Operating state "F12" is therefore very similar to operating "F1" with the difference of different measurement variables (here: speed of sound $c_S$ instead of density ρ).

In the "F13" operating state of the electrical switch 1, p/T, $c_S$, $p_A/T$, and $p_B/T$ decrease (symbol "↓"). While p/T, $c_S$, and $p_A/T$ decrease at specific rates, $p_B/T$ decreases at a higher rate than $p_A/T$ (large symbol "↓"). The trend variable for $p_A/p_B$ increases (symbol "↑"). This leads to the analysis conclusion "fault scenario: preferential leakage of component B for the electrical switch 1", which is a fault scenario which can be distinguished from all other mentioned fault scenarios and in which the true values of the characterizing variables $p_A/T$ and $p_B/T$ can be determined from the measurement variables p, $c_S$, and T. Operating state "F13" is therefore very similar to operating "F2" with the difference of different measurement variables (here: speed of sound $c_S$ instead of density $\rho$).

It should be pointed out that linked operating states (that are not explicitly mentioned here) for the respective other component exist for a plurality of the above mentioned operating states/fault scenarios. As an example, an operating state "F2'" exists for the fault scenario "preferential leakage of component A". As a difference to "F2", in "F2'" $p_A/T$ decreases at a higher rate than $p_B/T$ and $p_A/p_B$ decreases.

Definitions:

The term "aliphatic" relates to both "linear aliphatic" and "branched aliphatic".

The term "fluid" relates to "a substance, such as a liquid [and/] or gas, that can flow, has no fixed shape, and offers little resistance to an external stress" (from http://www.thefreedictionary.com/fluid, accessed on Sep. 11, 2011).

The term "physical state" of an insulation fluid refers to a plurality of physical and/or thermodynamic properties of the insulation fluid describing the state of the insulation fluid under a given set of physical conditions. Examples are suitable combinations of pressure p, density $\rho$, temperature T, viscosity $\eta$, thermal conductivity $\lambda$, and speed of sound $c_S$.

The term "concentration" herein shall define
  a quantity (with units) which is indicative of an amount per volume unit, e.g. a particle number per volume unit, moles per volume unit, or a number density, or
  a number (without units) which is indicative of a ratio such as a mole fraction, a pressure-normalized partial pressure, a volume fraction, a mass fraction, or a density fraction.

The term "high-voltage" relates to voltages larger than 50 kV.

The term "medium-voltage" relates to voltages larger than 1 kV.

As it is apparent from the description above, the term "method for operating a fluid-insulated electrical apparatus" relates to a method for making the electrical apparatus available and/or maintaining the operation of the electrical apparatus.

The compound class "hydrofluoroethers" relates to specific partially or fully fluorinated ethers as, e.g., available from 3M.

The compound "C5" particularly relates to a partially or fully fluorinated fluoroketone selected from the group consisting of the compounds defined by the following structural formulae in which at least one hydrogen atom, preferably all hydrogen atoms, is or are substituted with a fluorine atom orfluorine atoms:

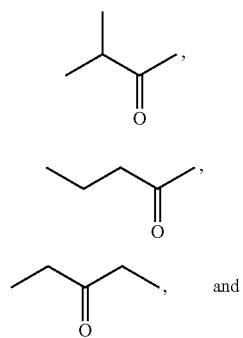

The compound "C6" particularly relates to a partially or fully fluorinated fluoroketone selected from the group consisting of the compounds defined by the following structural formulae in which at least one hydrogen atom, preferably all hydrogen atoms, is or are substituted with a fluorine atom/ fluorine atoms:

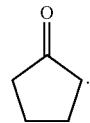

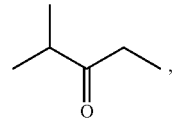

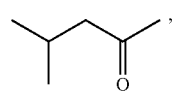

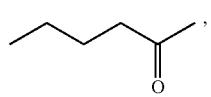

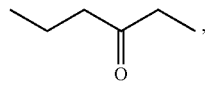

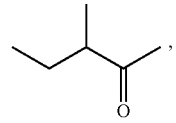

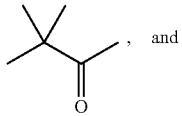

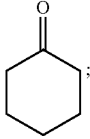

The compound "C7" particularly relates to a partially or fully fluorinated fluoroketone selected from the group consisting of the compounds defined by the following structural formulae in which at least one hydrogen atom, preferably all hydrogen atoms, is or are substituted with a fluorine atom/ fluorine atoms:

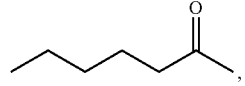

-continued

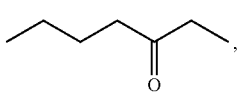 (IIIb),

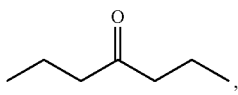 (IIIc),

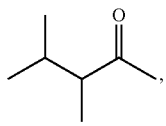 (IIId),

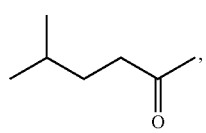 (IIIe),

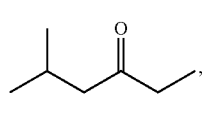 (IIIf),

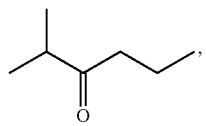 (IIIg),

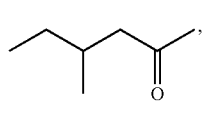 (IIIh),

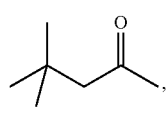 (IIIi),

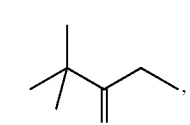 (IIIj),

 (IIIk),

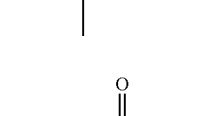 (IIIl),

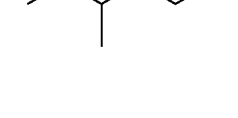 (IIIm),

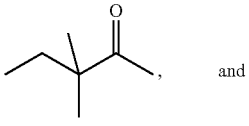, and

-continued

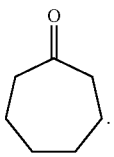 (IIIn).

Note:

While there are shown and described presently preferred or advantageous embodiments of the invention, it is to be distinctly understood that the invention is not limited thereto but may be otherwise variously embodied and practiced within the scope of the following claims. Therefore, terms like "preferred", "advantageous" or the like denote optional and exemplary features or embodiments only. Method step shall generally mean method element, i.e. does not imply that the steps shall be executed in the order as they are listed.

This application claims priority from the yet unpublished international patent applications PCT/EP2011/072510, PCT/EP2012/051688 and PCT/EP2012/067215, the content of which is hereby enclosed by reference in its entirety.

In an aspect of the invention, a method for operating a fluid-insulated electrical apparatus 1, in particular gas-insulated medium or high voltage switchgear, is disclosed wherein an insulation fluid 10 of the electrical apparatus 1 comprises at least a first component A and a second component B, the method comprising the method elements of:

at a first time determining a physical state of the insulation fluid 10 by measuring at least three measurement variables $\rho$, p, T, $\lambda$, $\eta$, $c_S$ by means of at least one sensor 30, wherein the measurement variables $\rho$, p, T, $\lambda$, $\eta$, $c_S$ are indicative of the physical state of the insulation fluid 10 at the first time, and wherein the measurement variables $\rho$, p, T, $\lambda$, $\eta$, $c_S$ are selected such that at least two characterizing variables indicative of partial pressures $p_A$, $p_B$ or concentrations $c_A$, $c_B$ of the first and the second components A, B of the insulation fluid 10 can be determined using the measurement variables $\rho$, p, T, $\lambda$, $\eta$, $c_S$, at a second time determining the physical state of the insulation fluid 10 by measuring the at least three measurement variables $\rho$, p, T, $\lambda$, $\eta$, $c_S$ by means of the at least one sensor 30, wherein the measurement variables $\rho$, p, T, $\lambda$, $\eta$, $c_S$ are indicative of the physical state of the insulation fluid 10 at the second time, and wherein the measurement variables $\rho$, p, T, $\lambda$, $\eta$, $c_S$ are selected such that at least two characterizing variables indicative of partial pressures $p_A$, $p_B$ or concentrations $c_A$, $c_B$ of the first and the second components A, B of the insulation fluid 10 can be determined using the measurement variables $\rho$, p, T, $\lambda$, $\eta$, $c_S$, and (i) deriving at least one trend variable for at least one of the measurement variables $\rho$, p, T, $\lambda$, $\eta$, $c_S$ using the at least one of the measurement variables $\rho$, p, T, $\lambda$, $\eta$, $c_S$ from the first and from the second time, wherein the at least one trend variable is indicative of a change of the at least one of the measurement variables $\rho$, p, T, $\lambda$, $\eta$, $c_S$ between the first and the second time; and/or (ii) at the first and at the second time deriving from at least one of the measurement variables $\rho$, p, T, $\lambda$, $\eta$, $c_S$ at least one of the characterizing variables from the first time and from the second time, wherein the at least one of the characterizing variables from the first time and from the second time is indicative of the physical state of the insulation fluid 10 at the first and at the second time, and deriving at least one trend variable for the at least one of the characterizing variables using the at least one of the characterizing variables from the first and from the second time, wherein the at least one trend variable is indicative of a change of the at least one of the characterizing variables between the first and the second time, wherein at least two trend variables are derived for the at least two characterizing variables indicative of the partial pressures $p_A$, $p_B$ or concentrations $c_A$, $c_B$ of the first and second components A, B of the insulation fluid 10, and the at least two characterizing variables are selected from the group consisting of: a function $f1(p_A)$, a function $f2(p_A/T)$, a function $f3(p_B)$, a function $f4(p_B/T)$, a function $f5(p_A, p_B)$, a function $f6(p_A, p_B, T)$, a function $f7(p_A/p_B)$, a function $f8(c_A)$, a function $f9(c_B)$, a function $f10(c_A, c_B)$, and a function $f11(c_A/c_B)$, with $p_A$ and $p_B$ being the partial pressures of the first and second components A, B of the insulation fluid 10, with $c_A$ and $c_B$ being the concentrations of the first and second components A, B of the insulation fluid 10, and with T being a temperature T of the insulation fluid 10; and determining, using the at least one trend variable for the at least one of the characterizing variables, an operating state O, F1 of the electrical apparatus 1 out of a group of at least two possible operating states O, F1.

REFERENCE NUMERALS

1: electrical apparatus
10: insulation fluid
A, B, C: components of the insulation fluid 10
$\rho$, p, T, $\lambda$, $\eta$, $c_S$: measurement variables
30: sensor
O, F1, F2: first, second, and third operating states of the electrical apparatus 1 corresponding to a first non-fault scenario, a first fault scenario, and a second fault scenario for the electrical apparatus 1
p: pressure of the insulation fluid 10
T: temperature of the insulation fluid 10
$\rho$: density of the insulation fluid 10
$\lambda$: thermal conductivity of the insulation fluid 10
$\eta$: viscosity of the insulation fluid 10
$c_S$: speed of sound in the insulation fluid 10
40: control and analysis unit
50: gas-tight compartment
60: electrically active part
70: component reservoir
80: heater
90: filter

The invention claimed is:

1. A method for operating a fluid-insulated electrical apparatus wherein an insulation fluid of the electrical apparatus comprises at least a first component and a second component, the method comprising the method elements of:

determining a physical state of the insulation fluid by measuring at least three measurement variables by means of at least one sensor, wherein the measurement variables are indicative of the physical state of the insulation fluid and wherein the measurement variables are selected such that at least two characterizing variables indicative of partial pressures ($p_A$, $p_B$) or concentrations ($c_A$, $c_B$) of the first component and the second component of the insulation fluid can be determined using the measurement variables, wherein the method comprises a further method element of: deriving at least one trend variable for at least one of the measurement variables, wherein the at least one trend variable is indicative of a change over time of the at least one measurement variable; and/or a further method element of: deriving from at least one of the measurement variables at least one of the characterizing variables, wherein the at least one of the characterizing variables is indicative of the physical state of the insulation fluid, and deriving at least one trend variable for the at least one of the characterizing variables, wherein the trend variable is indicative of a change over time of the at least one of the characterizing variables;

wherein at least two trend variables are derived for the at least two characterizing variables indicative of the partial pressures ($p_A$, $p_B$) or concentrations ($c_A$, $c_B c_B$) of the first and second components of the insulation fluid, and wherein the at least two characterizing variables are selected from the group consisting of: a function $f1(p_A)$, a function $f2(p_A/T)$, a function $f3(p_B)$, a function $f4(p_B/T)$, a function $f5(p_A, p_B)$, a function $f6(p_A, p_B, T)$, a function $f7(p_A/p_B)$, a function $f8(c_A)$, a function $f9(c_B)$, a function $f10(c_A, c_B)$, and a function $f11(c_A/c_B)$, with $p_A$ and $p_B$ being the partial pressures of the first and second components of the insulation fluid, with $c_A$ and $c_B$ being the concentrations of the first and second components of the insulation fluid, and with T being a temperature T of the insulation fluid;

wherein further the method comprises a method element of:

determining, using the at least one trend variable for the at least one of the characterizing variables, an operating state of the electrical apparatus out of a group of at least two possible operating states, wherein a first possible operating state of the electrical apparatus corresponds to a first fault scenario for the electrical apparatus and a second possible operating state of the electrical apparatus corresponds to a second fault scenario for the electrical apparatus; and wherein at least one of the first and second fault scenarios for the electrical apparatus is selected from the group consisting of:

uniform leakage of the insulation fluid, preferential leakage of the first or the second component of the insulation fluid, preferential condensation of the first or the second component of the insulation fluid, appearance of at least a third component in the insulation fluid, decomposition of at least the first or the second component of the insulation fluid, intermolecular reactions between molecules of the first and the second components of the insulation fluid, and removal of at least the first or the second component of the insulation fluid.

2. The method of claim 1, wherein the measurement variables are indicative of at least a pressure (p) and a temperature (T) of the insulation fluid.

3. The method of claim 2, wherein the measurement variables are indicative of at least the pressure (p), the temperature (T), and a density ($\rho$) of the insulation fluid.

4. The method of claim 3, comprising a method element of deriving at least one of the characterizing variables indicative of the partial pressures (pA, pB) or concentrations (cA, cB) for the first and/or for the second component of the insulation fluid, wherein at least one relating equation is used for deriving the at least one characterizing variable using the measurement variables, and wherein the relating equation or at least one of the relating equations is an equation of state which is selected from the group consisting of: ideal gas law, van-der- Waals equation of state, virial equation of state, Beattie-Bridgeman equation of state, and Peng-Robinson equation of state.

5. The method of claim 4, wherein the partial pressure ($p_A$) or the concentration ($c_A$) of the first component of the insulation fluid is at least a factor of 2 higher than the partial pressure ($p_B$) or concentration ($c_B$) of the second component of the insulation fluid, and/or
wherein one relating equation is used for deriving the characterizing variables indicative of the partial pressures ($P_A$, $p_B$) or concentrations ($c_A$, $c_B$) using the measurement variables for all components of the insulation fluid.

6. The method of claim 2, wherein the measurement variables are additionally indicative of at least one element of the group consisting of: a thermal conductivity ($\lambda$), a viscosity ($\eta$), and a speed of sound ($c_s$) in the insulation fluid.

7. The method of claim 1, comprising a method element of deriving at least one of the characterizing variables indicative of the partial pressures ($p_A$, $p_B$) or concentrations ($c_A$, $c_B$) for the first and/or for the second component of the insulation fluid, wherein
at least one relating equation is used for deriving the at least one characterizing variable using the measurement variables.

8. The method of claim 1, comprising a method element of deriving the at least two characterizing variables indicative of partial pressures ($p_A$, $p_B$) or concentrations ($c_A$, $c_B$) of the first and the second components of the insulation fluid, wherein at least one relating equation is used for deriving the characterizing variables using the measurement variables.

9. The method of claim 1, wherein the functions f1 ... f11 depend on additional variables; and/or wherein the functions f1 ... f11 are monotonous functions of their variables.

10. The method of claim 1, wherein the determining of the operating state comprises using the at least one trend variable for the at least one of the measurement variables.

11. The method of claim 1, wherein the second component is selected from the group consisting of:
sulfur hexafluoride,
partially or fully fluorinated ethers,
partially or fully fluorinated ketones, and
mixtures thereof, and
wherein the first component is selected from the group consisting of:
nitrogen,
oxygen,
carbon dioxide,
nitric oxide,
nitrogen dioxide,
nitrous oxide,
argon,
methanes,
air, and
mixtures thereof.

12. The method of claim 11, wherein the second component is selected from the group consisting of:
cyclic and/or aliphatic perfluoropentanones,
cyclic and/or aliphatic perfluorohexanones,
cyclic and/or aliphatic perfluoroheptanones,
sulfur hexafluoride, and
hydrofluoroethers.

13. The method of claim 11, wherein the second component is 1,1,1,3,4,4,4-heptafluoro-3-(tri-fluoro-methyl)butan-2-one.

14. The method of claim 11, wherein the second component is 1,1,1,2,4,4,5,5,5-nonafluoro-4-(tri-fluoromethyl)pentan-3-one.

15. The method of claim 11, wherein the second component is one of a hydrofluoroether, a hydrofluoro monoether, or a perfluoro monoether.

16. The method of claim 11, wherein the second component is one of a hydrofluoro monoether containing at least 3 carbon atoms or a perfluoro monoether containing at least 4 carbon atoms.

17. The method of claim 11, wherein the second component is one of a hydrofluoro monoketone, a perfluoro monoketone, or a mixture thereof.

18. The method according to claim 17, wherein the second component is a perfluoro monoketone comprising at least 5 carbon atoms.

19. The method according to claim 18, wherein the perfluoro monoketone comprises exactly 5 or 6 or 7 or 8 carbon atoms.

20. The method of claim 11, wherein the second component is selected from the group consisting of:
cyclic and/or aliphatic fluoropentanones,
cyclic and/or aliphatic fluorohexanones,
cyclic and/or aliphatic fluoroheptanones,
sulfur hexafluoride, and
hydrofluoroethers.

21. The method of claim 11, wherein the first component consists of
nitrogen and oxygen with relative partial pressures between $p(N_2)/(p(O_2)+p(N_2))=0.7$, $p(O_2)/(p(O_2)+p(N_2))=0.3$ and $p(N_2)/(p(O_2)+p(N_2))=0.95$, $p(O_2)/(p(O_2)+p(N_2))=0.05$, or
carbon dioxide and oxygen with relative partial pressures between $p(CO_2)/(p(O_2)+p(CO_2))=0.6$, $p(O_2)/(p(O_2)+p(CO_2))=0.4$ and $p(CO_2)/(p(O_2)+p(CO_2))=0.99$, $p(O_2)/(p(O_2)+p(CO_2))=0.01$, or
carbon dioxide and nitrogen with relative partial pressures between $p(CO_2)/(p(N_2)+p(CO_2))=0.1$, $p(N_2)/(p(N_2)+p(CO_2))=0.9$ and $p(CO_2)/(p(N_2)+p(CO_2))=0.9$, $p(N_2)/(p(N_2)+p(CO_2))=0.1$, and
wherein the second component comprises at least one of the group consisting of:
1,1,1,3,4,4,4-heptafluoro-3-(tri-fluoro-methyl)butan-2-one with a partial pressure between 0.1 bar and 0.7 bar at a temperature of 20° C.,
1,1,1,2,4,4,5,5,5-nonafluoro-4-(tri-fluoromethyl)pentan-3-one with a partial pressure between 0.01 bar and 0.3 bar at a temperature of 20° C.,
sulfur hexafluoride with a partial pressure between 0.1 bar and 2 bar at a temperature of 20° C., and
hydrofluoroethers with a partial pressure between 0.2 bar and 1 bar at a temperature of 20° C.

22. The method of claim 11, wherein the first component comprises
nitrogen and oxygen with relative partial pressures between $p(N_2)/(p(O_2)+p(N_2))=0.75$, $p(O_2)/(p(O_2)+p(N_2))=0.25$ and $p(N_2)/(p(O_2)+p(N_2))=0.90$, $p(O_2)/(p(O_2)+p(N_2))=0.10$, and
wherein the second component comprises 1,1,1,3,4,4,4-heptafluoro-3-(tri-fluoromethyl)bu-tan-2-one with a partial pressure between 0.25 bar and 0.5 bar and/or the component 1,1,1,2,4,4,5,5,5-nona-fluoro-4-(tri-fluoromethyl)pentan-3-one with a partial pressure between 0.02 bar and 0.3 bar at a temperature of 20° C.

23. The method of claim 1, further comprising the method element of issuing a signal when the electrical apparatus enters or leaves a possible operating state, wherein the signal is an alert signal.

24. The method of claim 23, further comprising the method element of shutting down the electrical apparatus.

25. The method of claim 1, further comprising a method element of circulating the insulation fluid for homogenizing a density and/or a mixture of the first and/or second components before carrying out the method element of measuring the at least three measurement variables.

26. A fluid-insulated electrical apparatus, comprising:
an insulation fluid, the insulation fluid comprising at least two components,
at least one sensor for measuring at least three measurement variables indicative of a physical state of the insulation fluid, and
a control and analysis unit adapted to carry out the method elements of a method of claim 1 for operating the fluid-insulated electrical apparatus.

27. The electrical apparatus of claim 26, wherein the control and analysis unit is furthermore adapted to issue an alert signal when the electrical apparatus enters or leaves a possible operating state.

28. The electrical apparatus of claim 26, wherein the control and analysis unit is furthermore adapted to shut down the electrical apparatus.

29. The electrical apparatus of any of the claims 26 to 28, wherein the control and analysis unit is furthermore adapted to distinguish at least a first, a second, and a third operating state out of a plurality of possible operating states of the electrical apparatus,
wherein at least the second and the third operating states correspond to a first and second fault scenario for the electrical apparatus.

30. The apparatus according to claim 26, wherein the fluid-insulated voltage electrical apparatus is a gas-insulated medium or high voltage switchgear.

31. The method of claim 1, wherein trend variables are derived at least for measurement variables or characterizing variables indicative of $p/T$, $p_A/T$, $p_B/T$, and $p_A/p_B$ of the insulation fluid with p being a pressure and T being the temperature of the insulation fluid, and with $p_A$ and $p_B$ being the partial pressures of the first and second components of the insulation fluid, or
wherein trend variables are derived at least for measurement variables or characterizing variables indicative of $p/T$, $c_A$, $c_B$, and $c_A/c_B$ of the insulation fluid with p being the pressure and T being the temperature of the insulation fluid, and with $c_A$, $c_B$ being the concentrations of the first and second components of the insulation fluid.

32. The method of any one of the claims 1, 6, 8, and 9, wherein:
trend variables are derived at least for measurement variables or characterizing variables indicative of $p/T$, $p_A/T$, $p_B/T$, and $p_A/p_B$ of the insulation fluid with p being a pressure and T being the temperature of the insulation fluid, and with $p_A$ and $p_B$ being partial pressures or the partial pressures of the first and second components of the insulation fluid, or trend variables are derived at least for measurement variables or characterizing variables indicative of $p/T$, $c_A$, $c_B$, and $c_A/c_B$ of the insulation fluid with p being the pressure and T being the temperature of the insulation fluid, and with $c_A$, $c_B$ being concentrations or the concentrations of the first and second components of the insulation fluid; and a trend variable is derived for one of the measurement variables indicative of $\rho$ with $\rho$ being a density of the insulation fluid, and
wherein the method further comprises the method element of testing if a) the trend variables for $p/T$, $\rho$, $p_A/T$, and $p_B/T$ are <0 and the trend variable for $p_A/p_B$ is equal to 0 with $\rho$ being the density of the insulation fluid, and/or testing if
b) the trend variables for $p/T$, $\rho$, $c_A$, and $c_B$ are <0 and the trend variable for $c_A/c_B$ is equal to 0, and/or testing if
c) the trend variables for $p/T$, $\rho$, $p_A/T$, and $p_B/T$ are <0 and the trend variable for $p_A/p_B$ is >0, and/or testing if
d) the trend variables for $p/T$, $\rho$, $c_A$, and $c_B$ are <0 and the trend variable for $c_A/c_B$ is >0, and/or testing if
e) the trend variables for $p/T$, $\rho$, $p_A/T$, and $p_A/p_B$ are <0 and the trend variable for $p_B/T$ is equal to 0, and/or testing if
f) the trend variables for $p/T$, $\rho$, $c_A$, and $c_A/c_B$ are <0 and the trend variable for $c_B$ is equal to 0, and/or testing if
g) the trend variables for $p/T$, $\rho$, and $p_B/T$ are >0 and the trend variables for $p_A/T$ and $p_A/p_B$ are <0, and/or testing if
h) the trend variables for $p/T$, $\rho$, and $C_B$ are >0 and the trend variables for $c_A$ and $c_A/c_B$ are <0, and/or testing if
i) the trend variables for $p/T$ and $p_B/T$ are >0, the trend variables for $p_A/T$ and $p_A/p_B$ are <0, and the trend variable for $\rho$ is equal to 0, and/or testing if
j) the trend variables for $p/T$ and $C_B$ are >0, the trend variables for $c_A$ and $c_A/c_B$ are <0, and the trend variable for $\rho$ is equal to 0, and/or testing if
k) the trend variables for $p/T$, $\rho$, $p_A/T$, $p_B/T$ and $p_A/p_B$ are equal to 0, and/or testing if
l) the trend variables for $p/T$, $\rho$, $c_A$, $C_B$, and $c_A/c_B$ are equal to 0.

33. The method according to claim 1, wherein the fluid-insulated voltage electrical apparatus is a gas-insulated medium or high voltage switchgear.

34. A method for operating a fluid-insulated electrical apparatus wherein an insulation fluid of the electrical apparatus comprises at least a first component and a second component, the method comprising the method elements of:
determining a physical state of the insulation fluid by measuring at least three measurement variables by means of at least one sensor, wherein the measurement variables are indicative of the physical state of the insulation fluid and wherein the measurement variables are selected such that at least two characterizing variables indicative of partial pressures ($p_A$, $p_B$) or concentrations ($c_A$, $c_B$) of the first component and the second component of the insulation fluid can be determined using the measurement variables,
wherein the method comprises a further method element of: deriving at least one trend variable for at least one of the measurement variables, wherein the at least one trend variable is indicative of a change over time of the at least one measurement variable; and/or a further method element of: deriving from at least one of the measurement variables at least one of the characterizing variables, wherein the at least one of the characterizing variables is indicative of the physical state of the insulation fluid, and deriving at least one trend variable for the at least one of the characterizing variables, wherein the trend variable is indicative of a change over time of the at least one of the characterizing variables;
wherein at least two trend variables are derived for the at least two characterizing variables indicative of the partial pressures ($p_A$, $p_B$) or concentrations ($c_A$, $c_B$) of the first and second components of the insulation fluid, and
wherein the at least two characterizing variables are selected from the group consisting of: a function $f1(p_A)$, a function f2($p_A$/T), a function f3($p_B$), a function f4($p_B$/T), a function f5($p_A$, $p_B$), a function f6($p_A$, $p_B$, T), a function f7($p_A$/$p_B$), a function f8($c_A$), a function f9($c_B$), a function f10($c_A$, $c_B$), and a function f11($c_A$/$c_B$), with $p_A$ and $p_B$ being the partial pressures of the first and second components of the insulation fluid, with $c_A$ and $c_B$ being the concentrations of the first and second components of the insulation fluid, and with T being a temperature T of the insulation fluid;

wherein further the method comprises a method element of:

determining, using the at least one trend variable for the at least one of the characterizing variables, an operating state of the electrical apparatus out of a group of at least two possible operating states, wherein trend variables are derived at least for measurement variables or characterizing variables indicative of p/T, $p_A$/T, $p_B$/T, and $p_A$/$p_B$ of the insulation fluid with p being a pressure and T being a temperature of the insulation fluid, and with $P_A$ and $P_B$ being the partial pressures of the first and second components of the insulation fluid, or wherein trend variables are derived at least for measurement variables or characterizing variables indicative of p/T, $c_A$, $c_B$, and $c_A$/$c_B$ of the insulation fluid with p being the pressure and T being the temperature of the insulation fluid, and with $c_A$, $c_B$ being the concentrations of the first and second components of the insulation fluid, wherein a trend variable is derived for one of the measurement variables indicative of ρ with ρ being a density of the insulation fluid, and wherein the method further comprises the method element of testing if a) the trend variables for p/T, ρ, $p_A$/T, and $p_B$/T are <0 and the trend variable for $p_A$/$p_B$ is equal to 0 with ρ being the density of the insulation fluid, and/or testing if b) the trend variables for p/T, ρ, $c_A$, and $c_B$ are <0 and the trend variable for $c_A$/$c_B$ is equal to 0, and/or testing if c) the trend variables for p/T, ρ, $p_A$/T, and $p_B$/T are <0 and the trend variable for $p_A$/$p_B$ is >0, and/or testing if d) the trend variables for p/T, ρ, $c_A$, and $c_B$ are <0 and the trend variable for $c_A$/$c_B$ is >0, and/or testing if e) the trend variables for p/T, ρ, $p_A$/T, and $p_A$/$p_B$ are <0 and the trend variable for $p_B$/T is equal to 0, and/or testing if f) the trend variables for p/T, ρ, $c_A$, and $c_A$/$c_B$ are <0 and the trend variable for $c_B$ is equal to 0, and/or testing if g) the trend variables for p/T, ρ, and $p_B$/T are >0 and the trend variables for $p_A$/T and $p_A$/$p_B$ are <0, and/or testing if h) the trend variables for p/T, ρ, and $c_B$ are >0 and the trend variables for $c_A$ and $c_A$/$c_B$ are <0, and/or testing if i) the trend variables for p/T and $p_B$/T are >0, the trend variables for $p_A$/T and $p_A$/$p_B$ are <0, and the trend variable for ρ is equal to 0, and/or testing if j) the trend variables for p/T and $c_B$ are >0, the trend variables for $c_A$ and $c_A$/$c_B$ are <0, and the trend variable for ρ is equal to 0, and/or testing if k) the trend variables for p/T, ρ, $p_A$/T, $p_B$/T and $p_A$/$p_B$ are equal to 0, and/or testing if l) the trend variables for p/T, ρ, $c_A$, $C_B$, and $c_A$/$c_B$ are equal to 0.

35. A method for operating a fluid-insulated electrical Apparatus wherein an insulation fluid of the electrical apparatus comprises at least a first component and a second component, the method comprising the method elements of:

determining a physical state of the insulation fluid by measuring at least three measurement variables by means of at least one sensor, wherein the measurement variables are indicative of the physical state of the insulation fluid and wherein the measurement variables are selected such that at least two characterizing variables indicative of partial pressures ($p_A$, $p_B$) or concentrations ($c_A$, $c_B$) of the first component and the second component of the insulation fluid can be determined using the measurement variables, wherein the method comprises a further method element of: deriving at least one trend variable for at least one of the measurement variables, wherein the at least one trend variable is indicative of a change over time of the at least one measurement variable; and/or a further method element of: deriving from at least one of the measurement variables at least one of the characterizing variables, wherein the at least one of the characterizing variables is indicative of the physical state of the insulation fluid, and deriving at least one trend variable for the at least one of the characterizing variables, wherein the trend variable is indicative of a change over time of the at least one of the characterizing variables;

wherein at least two trend variables are derived for the at least two characterizing variables indicative of the partial pressures ($p_A$, $p_B$) or concentrations ($c_A$, $c_B$) of the first and second components of the insulation fluid, and wherein the at least two characterizing variables are selected from the group consisting of: a function f1($p_A$), a function f2($p_A$/T), a function f3($p_B$), a function f4($p_B$/T), a function f5($p_A$, $p_B$), a function f6($p_A$, $p_B$, T), a function f7($p_A$/$p_B$), a function f8($c_A$), a function f9($c_B$), a function f10($c_A$, $c_B$), and a function f11($c_A$/$c_B$), with $p_A$ and $p_B$ being the partial pressures of the first and second components of the insulation fluid, with $c_A$ and $c_B$ being the concentrations of the first and second components of the insulation fluid, and with T being a temperature T of the insulation fluid;

wherein further the method comprises a method element of:

determining, using the at least one trend variable for the at least one of the characterizing variables, an operating state of the electrical apparatus out of a group of at least two possible operating states, wherein a trend variable is derived for one of the measurement variables indicative of ρ with ρ being a density of the insulation fluid, and wherein the method further comprises the method element of testing if a) the trend variables for p/T, ρ, $p_A$/T, and $p_B$/T are <0 and the trend variable for $p_A$/$p_B$ is equal to 0 with ρ being the density of the insulation fluid, and/or testing if b) the trend variables for p/T, ρ, $c_A$, and $c_B$ are <0 and the trend variable for $c_A$/$c_B$ is equal to 0, and/or testing if c) the trend variables for p/T, ρ, $p_A$/T, and $p_B$/T are <0 and the trend variable for $p_A$/$p_B$ is >0, and/or testing if d) the trend variables for p/T, ρ, $c_A$, and $c_B$ are <0 and the trend variable for $c_A$/$c_B$ is >0, and/or testing if e) the trend variables for p/T, ρ, $p_A$/T, and $p_A$/$p_B$ are <0 and the trend variable for $p_B$/T is equal to 0, and/or testing if f) the trend variables for p/T, ρ, $c_A$, and $c_A$/$c_B$ are <0 and the trend variable for $c_B$ is equal to 0, and/or testing if g) the trend variables for $p/T$, $\rho$, and $p_B/T$ are >0 and the trend variables for $p_A/T$ and $p_A/p_B$ are <0, and/or testing if h) the trend variables for $p/T$, $\rho$, and $c_B$ are >0 and the trend variables for $c_A$ and $c_A/c_B$ are <0, and/or testing if i) the trend variables for $p/T$ and $p_B/T$ are >0, the trend variables for $p_A/T$ and $p_A/p_B$ are <0, and the trend variable for $\rho$ is equal to 0, and/or testing if j) the trend variables for $p/T$ and $c_B$ are >0, the trend variables for $c_A$ and $c_A/c_B$ are <0, and the trend variable for $\rho$ is equal to 0, and/or testing if k) the trend variables for $p/T$, $\rho$, $p_A/T$, $p_B/T$ and $p_A/p_B$ are equal to 0, and/or testing if l) the trend variables for $p/T$, $\rho$, $c_A$, $C_B$, and $c_A/c_B$ are equal to 0.

36. The method of any one of the claims 1, 35, and 11, further comprising at least one method element of the group consisting of:
increasing at least one of the partial pressures ($p_A$, $p_B$) or at least one of the concentrations ($c_A$, $c_B$) of the first and/or the second component of the insulation fluid by means of injecting an amount of the first and/or the second component from a component reservoir into a compartment of the electrical apparatus,
reducing at least one partial pressure ($p_A$, $p_B$) or at least one of the partial pressures ($p_A$, $p_B$) or at least one concentration ($c_A$, $c_B$) or at least one of the concentrations ($c_A$, $c_B$) of the first and/or the second component of the insulation fluid,
reducing a concentration of at least one contaminant in the insulation fluid by means of a filter,
at least partially evaporating a condensed amount of at least the first and/or the second component of the insulation fluid by means of a heater, and
condensing an amount of the first and/or of the second component of the insulation fluid by means of a cooler.

37. The method according to any one of the claims 1, 34, and 35, wherein at least one of the measurement variables is measured in a gaseous phase of the insulation fluid by means of the sensor, wherein the gaseous phase of the insulation fluid comprises a gaseous mixture of the first and the second components of the insulation fluid.

38. The method of claim 35, wherein the second component is selected from the group consisting of:
sulfur hexafluoride,
partially or fully fluorinated ethers,
partially or fully fluorinated ketones, and
mixtures thereof, and
wherein the first component is selected from the group consisting of:
nitrogen,
oxygen,
carbon dioxide,
nitric oxide,
nitrogen dioxide,
nitrous oxide,
argon,
methanes,
air, and
mixtures thereof.

39. The method of claim 35, wherein the measurement variables are indicative of at least a pressure (p), a temperature (T), and a density ($\rho$) of the insulation fluid.

40. The method of claim 39, wherein the measurement variables are additionally indicative of at least one element of the group consisting of: a thermal conductivity ($\lambda$), a viscosity ($\eta$), and a speed of sound ($c_s$) in the insulation fluid.

41. The method of claim 35, further comprising the method element of issuing a signal when the electrical apparatus enters or leaves a possible operating state, wherein the signal is an alert signal.

42. The method of claim 35, further comprising a method element of circulating the insulation fluid for homogenizing a density and/or a mixture of the first and/or second components before carrying out the method element of measuring the at least three measurement variables.

43. A fluid-insulated electrical apparatus, comprising:
an insulation fluid, the insulation fluid comprising at least two components,
at least one sensor for measuring at least three measurement variables indicative of a physical state of the insulation fluid, and
a control and analysis unit adapted to carry out the method elements of a method of claim 35 for operating the fluid-insulated electrical apparatus.

* * * * *